United States Patent [19]

Louw

[11] Patent Number: 4,533,345
[45] Date of Patent: Aug. 6, 1985

[54] UTERINE CATHETER

[75] Inventor: John A. Louw, Temecula, Calif.

[73] Assignee: Fertility & Genetics Associates, Chicago, Ill.

[21] Appl. No.: 504,282

[22] Filed: Jun. 14, 1983

[51] Int. Cl.³ .............................................. A61M 3/00
[52] U.S. Cl. ....................................... 604/43; 604/173; 604/268
[58] Field of Search .................. 604/43, 173, 170, 280, 604/264, 268, 39, 35

[56] References Cited

U.S. PATENT DOCUMENTS

| | | | |
|---|---|---|---|
| Re. 27,310 | 3/1972 | Hakim | 128/350 R |
| 914,950 | 3/1909 | Harris . | |
| 1,045,326 | 11/1912 | Ruflin | 604/43 |
| 1,581,508 | 4/1926 | Bomhard . | |
| 2,220,493 | 11/1940 | Pixler | 27/24 |
| 2,845,930 | 12/1958 | Brown | 128/348 |
| 3,095,871 | 7/1963 | Mann et al. | 128/2 |
| 3,101,545 | 8/1963 | Baughan | 32/33 |
| 3,421,510 | 1/1969 | Kettenbach | 128/350 |
| 3,448,739 | 6/1969 | Stark et al. | 128/2.05 |
| 3,460,540 | 8/1969 | Gagne | 128/349 |
| 3,467,103 | 9/1969 | McKinstry et al. | 128/349 |
| 3,503,385 | 3/1970 | Stevens | 128/2 |
| 3,506,010 | 4/1970 | Murr et al. | 128/276 |
| 3,516,410 | 6/1970 | Hakim | 604/268 |
| 3,527,203 | 9/1970 | Gravlee | 128/2 |
| 3,528,427 | 9/1970 | Sheridan et al. | 128/350 |
| 3,636,940 | 1/1972 | Gravlee | 128/2 B |
| 3,687,806 | 11/1972 | Bovenkamp | 195/1.8 |
| 3,777,743 | 12/1973 | Binard et al. | 128/2 B |
| 3,811,424 | 6/1974 | Dickinson et al. | 128/1 R |
| 3,811,443 | 5/1974 | Dickinson et al. | 128/235 |
| 3,828,781 | 8/1974 | Rothman | 128/278 |
| 3,854,470 | 12/1974 | Augspurger | 128/1 R |
| 3,866,598 | 2/1975 | Augspurger | 128/1 R |
| 3,889,657 | 6/1975 | Baumgarten | 128/2 B |
| 3,906,929 | 9/1975 | Augspurger | 128/1 |
| 3,913,577 | 10/1975 | Nehra et al. | 128/276 |
| 3,948,270 | 4/1976 | Hasson | 128/348 |
| 4,004,588 | 1/1977 | Alexander | 128/241 |
| 4,068,664 | 1/1978 | Sharp et al. | 128/276 |
| 4,089,337 | 5/1978 | Kronner | 128/348 |
| 4,139,012 | 2/1979 | Zahorsky | 128/350 R |
| 4,158,916 | 6/1979 | Adler | 32/33 |
| 4,178,936 | 12/1979 | Newcomb | 128/349 B |
| 4,182,328 | 1/1980 | Bolduc et al. | 128/235 |
| 4,193,392 | 3/1980 | Barnett | 128/1 R |
| 4,213,461 | 7/1980 | Pevsner | 128/348 |
| 4,280,500 | 7/1981 | Ono | 128/348 |
| 4,321,921 | 3/1982 | Laszczower | 128/276 |
| 4,326,505 | 4/1982 | Cropsey | 128/1 R |
| 4,468,216 | 8/1984 | Muto | 604/43 |

FOREIGN PATENT DOCUMENTS

| | | | |
|---|---|---|---|
| 790091 | 9/1935 | France | 128/747 |
| 2070437 | 2/1981 | United Kingdom . | |

OTHER PUBLICATIONS

J. Randal, "Transferring the Cell of Life", *Science Year* (1980), pp. 185–195.

*Primary Examiner*—Stephen C. Pellegrino
*Attorney, Agent, or Firm*—James F. Haley, Jr.; Margaret A. Pierri

[57] ABSTRACT

The present invention is directed to an apparatus for use in non-surgical procedures for treating the human uterus. The apparatus of the invention, called a uterine catheter, is of flexible, non-rigid construction which possesses sufficient stiffness to permit introduction of the device into the body by itself, without the need for rigid stylet or stiffening rod introduction means.

17 Claims, 2 Drawing Figures

UTERINE CATHETER

TECHNICAL FIELD

This invention relates to an improved apparatus for use in non-surgical procedures for treating the human uterus. The apparatus of the invention, designated a uterine catheter, may be used for the non-surgical recovery step of methods for human embryo transfer or artificial embryonation, flushing or probing the uterus, introducing treatment materials into the uterus, or diagnostic procedures. Preferably, the apparatus is used for non-surgical human embryo recovery in processes for human embryo transfer and artificial embryonation.

BACKGROUND OF THE INVENTION

Presently available apparatus designed for use in treating the human uterus are typically rigid devices. Such apparatus may cause discomfort to the patient and can lead to perforation of internal tissues. Additionally, the use of such rigid tools may require dilation of the cervix, repositioning of the uterus and use of clamps for stabilization. These procedures are often painful and can induce uterine bleeding.

U.S. Pat. No. 3,527,203 refers to an apparatus for irrigating a body cavity which has an inlet tube, an outlet tube, and a sealing member. The tubes are made from a rigid plastic material, and have rough-edged apertures which are designed to facilitate the collection of tissue samples.

U.S. Pat. No. 3,948,270 refers to a uterine cannula for human uterine elevation, which comprises a rigid tube positioned inside a Foley catheter. Due to its rigidity, this type of cannula cannot follow the natural contours of the uterus.

U.S. Pat. No. 3,095,871 refers to a diagnostic tool for the human uterus. The tool comprises a hard rubber catheter, used in combination with a rigid stylet introducer.

Rigid uterine-invasive apparatus are also used in the field of animal husbandry. For example, U.S. Pat. No. 3,854,470 refers to a rigid pipette containing a catheter for the insertion of ova into hooved mammals. U.S. Pat. Nos. 4,178,936 and 4,004,588 refer to uterine catheters, used in combination with rigid introducers that penetrate the uterus for ova recovery, particularly in cattle.

A non-rigid catheter has been developed to facilitate non-surgical procedures for treating the human uterus. This apparatus causes virtually no discomfort to the patient and does not require the use of external introduction means or anesthesia. This apparatus combines stiffness and flexibility to good advantage in such non-surgical procedures.

Although this non-rigid catheter can be employed in the recovery of pre-implantation embryos for human embryo transfer or artificial embryonation, it is somewhat disadvantaged in those applications because in operation it may lose lavage fluid out the oviducts and it may become obstructed by uterine tissue or mucus and, when obstructed may cause the loss of lavage fluid out the cervix. Any loss of such lavage fluid risks loss of the embryo. Moreover, when the fluid loss is through the oviducts an ectopic pregnancy may result. In addition, this catheter is not steerable within the uterine cavity, making it difficult to lavage the complete uterine surface. As a result, the recovery of pre-implantation embryos is lower than desired using this catheter.

Because of the pre-implantation embryo recovery efficiency of that catheter in processes for non-surgical human embryo transfer and artificial embryonation is lower than desired, the full potential of those processes in treating human infertility, in avoiding genetic or hereditary diseases and in permitting prenatal adoptions has not been fully realized.

SUMMARY OF THE INVENTION

The present invention is directed to an improved apparatus for use in non-surgical procedures for treating the human uterus. The apparatus of the invention, designated a uterine catheter, is of flexible, semi-rigid construction. It is characterized by ease of insertion without clogging with mucus or endometrial cells during entry through the cervix, the ability to lavage substantially all of the uterine surface, and a high percent recovery of the lavage fluid without clogging, thereby minimizing any loss of lavage fluid through the oviducts or cervix. Moreover, the recovered lavage fluid is usually clear and because it is free of blood and cellular debris it makes easier the location of any pre-implantation embryo.

GENERAL DESCRIPTION OF THE INVENTION

Figure 1:
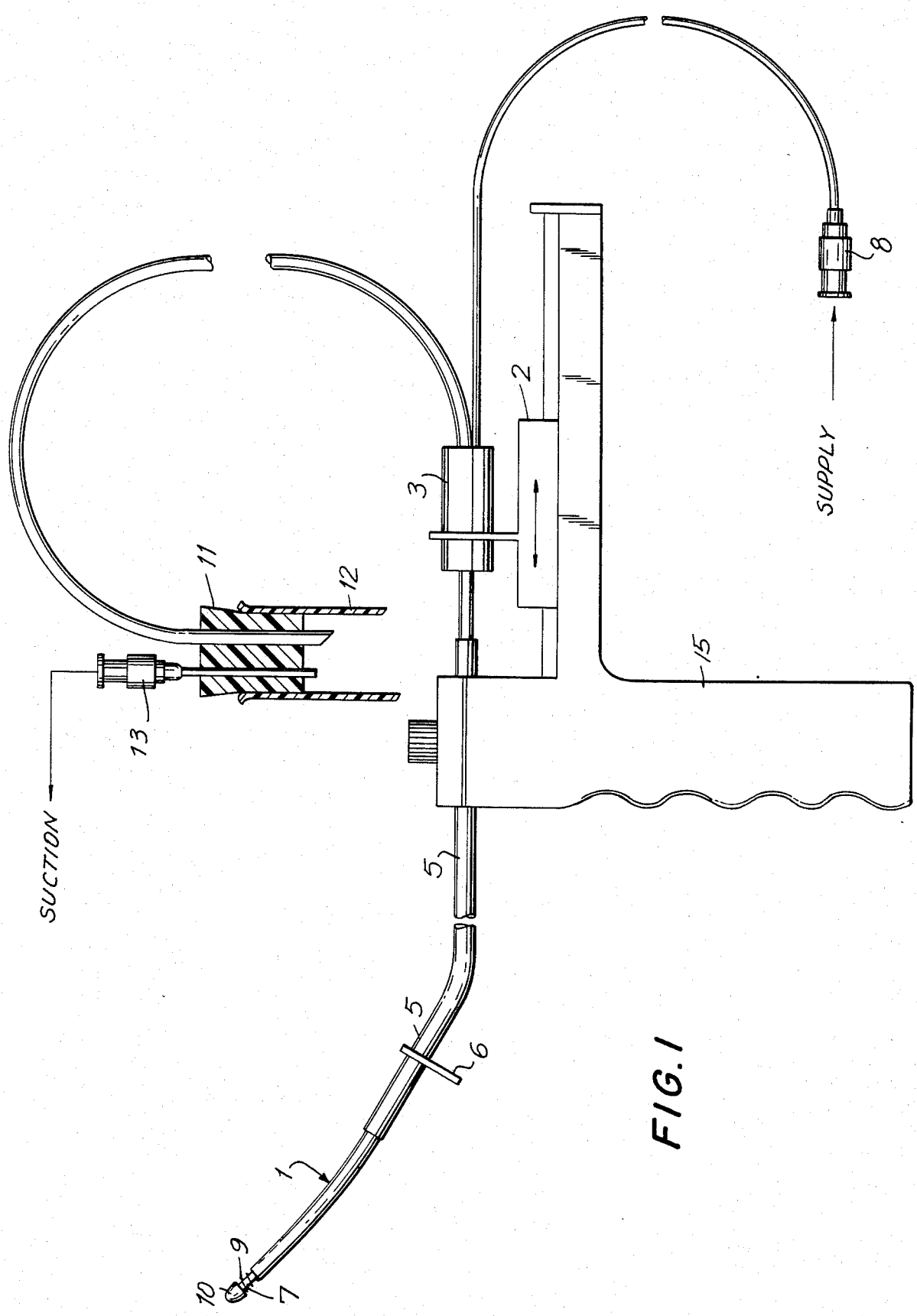
FIG. 1 is an elevational view of one embodiment of an improved double lumen catheter of the invention.

The uterine catheter of the present invention can be used for a variety of non-surgical procedures for treating the uterus. For example, the uterine catheter can be used for probing the uterus, non-surgically recovering pre-implantation embryos, flushing the uterus, testing for tubal patency, introducing a treating material into the uterus, and sampling endometrial or uterine tissue.

The uterine catheter of the present invention is particularly useful in the recovery of pre-implantation embryos in processes for non-surgical human embryo transfer and artificial embryonation. In the processes of human embryo transfer and artificial embryonation, which, for example, permit the non-surgical transfer of pre-implantation embryos from a human female donor to a human female recipient, the uterine catheter of this invention is used as a flushing tool. It introduces and recovers lavage fluid containing the pre-implantation embryo. Positive fluid pressure is used to introduce the lavage fluid into the uterus, and a negative pressure is used to remove this fluid and the embryo from the uterus.

Alternatively, the improved catheter of this invention may be employed in a method for flushing the uterine cavity with a variety of solutions as a method of birth control.

In all of the above described procedures, the novel and improved uterine catheter of the present invention can be inserted using the natural position of the cervix and uterus, without the use of clamps or any other type of positioning tool. The procedures are virtually painless to the patient being treated.

The improved catheter of this invention facilitates non-surgical procedures for treating the uterus with minimal discomfort to the patient. The catheter is made of a semi-rigid, slippery material which permits it to move smoothly, but deliberately through the cervix, and it has sufficient flexibility to enable it to conform to the uterine contours.

The improved uterine catheter of the invention comprises (a) at least two lumens at the forward distal end defined by an external tube and at least one internal tube, the tubes being coaxial to each other; (b) a forward distal end adapted for insertion into the human cervical canal and endometrial cavity and having a closed rounded tip, said tip being adjacent to the forward distal end of the inner tube(s); (c) a cage attached distally to said closed tip and proximally to the distal end of the external tube, the cage surrounding the distal most end of the inner tube(s) which are located coaxially therein, said distal most end of the inner tube(s) having means for delivering lavage fluid to the uterine cavity; (d) a rear proximal end, said end being adapted to permit separate connection of the inner and outer tubes to a fluid supply and a recovery reservoir; said catheter having an exterior diameter of about 7 to 16 French and having a combination of flexibility and stiffness sufficient to allow the catheter to describe a 10° to 30° angle per six centimeters when inserted into the uterine cavity to conform to uterine contours and to be steerable within the uterine cavity.

The catheter may be of materials such as polyvinyl chloride, polyethylene, or Teflon ®(tetrafluoroethylene). The preferred catheter is transparent in order to permit observation of fluid contents and motion while the uterine catheter is in use. It may also be desirably coated with Teflon ®, a silicone, or a similar slippery resin.

The uterine catheter of the present invention has a small diameter which permits ready positioning through the cervical os and into the uterus. The catheter is preferably a two lumen device. The exterior diameter of the catheter is preferably between about 7 French to 16 French and more preferably 11 French. The uterine catheter is generally about 30 cm in length.

The relative flow of liquid through the lumens of the catheter at working pressures is important. The supply lumen(s) must not provide fluid at a rate substantially greater than that removed by the suction lumen(s). Neither should the suction lumen(s) recover fluid at a rate substantially greater than that supplied by the supply lumen(s). Preferably, the rates of supply and recovery substantially are the same. To accomplish this equalization of supply and recovery, we regulate the pressure of the liquid flow and the size of the lumens. In the preferred embodiment of this invention the flow is adjusted to accommodate a ratio of diameters of suction lumen to supply lumen of between 5:1 and 15:1.

The tubes which define the lumens should be made of resilient, flexible, smooth material, e.g., Teflon ®(tetrafluoroethylene), polyvinylchloride or polyethylene. The inner surface of the suction lumen defined by the inner and outer tubes should be slippery enough to permit uninterrupted fluid flow and to avoid loss of embryos due to sticking to the tube surfaces. This may be accomplished by treating the tube walls with silicone sprays or other methods known in the art. It should be understood that any catheter construction having at least two lumens is within the scope of this invention so long as at the forward distal end of the catheter the lumens are defined by an external tube and at least one internal tube.

The closed rounded tip is hard. It may be constructed of high impact plastic or resin or metal. It preferably is bullet shaped. In one preferred embodiment of this invention, the tip is attached to the forward distal end of the inner tube.

The cage may be of any design or material which is sufficient to protect the space defined by the cage from obstruction by mucus and/or endometrium during treatment of the uterine cavity with liquid and the recovery of that liquid. For example, the cage may be of a helical or a ribbed design and be constructed of a preferably non-corrosive, rigid material, such as stainless steel.

In a preferred embodiment of this invention, the means for delivering lavage fluid are radial spray holes in the distal most end of the inner tube protected by the cage having a diameter of between about 0.003 and 0.020 inches. While they may be located randomly along the distal most end of the inner tube, we prefer to locate them adjacent the point where the distal end of the inner tube is connected to the rounded tip. In that location we believe the uterine lavage and embryo recovery is most effective. The holes are located in such a manner as to prevent uterine lavage spray from hitting the structural members that define the cage.

The catheter should have a combination of flexibility and stiffness sufficient to describe a 10° to 30° angle per six centimeters when inserted into the uterine cavity, to allow it to conform to the uterine contours and to be steerable within the uterine cavity. We prefer to use catheters for recovery of pre-implantation embryos whose flexibility and stiffness are defined as two inches of catheter clamped on one end deflecting at the free end 0.2 inches under loads ranging from 0.5 to 2.5 oz. We also prefer to use catheters that describe a 10° to 30° angle, and more preferably a 15° angle, per six centimeters before insertion into the uterine cavity.

The improved catheter of this invention may be used both with, and without, an accompanying guide or catheter sleeve. Preferably, when the catheter is used for embryo recovery, a guide is employed. The guide has four major functions: (1) to stabilize the catheter during its application to the cervix; (2) to provide a shield for the cage of the catheter during insertion through the cervix, thereby preventing the tip from becoming clogged with cervical secretions; (3) to gauge easily uterine depth, thereby preventing potentially damaging deep penetration of the catheter into the uterine cavity; and (4) to transmit rotary motion to the catheter, allowing the operator to sweep substantially all of the uterine surface.

The optional guide or catheter sleeve is about 8 to 17 French in external diameter. It is made of a rigid material, e.g., copper, brass, stainless steel or rigid plastic. It is about 10 to 14 cm in length. The guide also has a locator flange positioned about 2 to 2.5 cm from the forward distal end of the guide. The flange, which is usually perpendicular to the sleeve, is positioned so as to come to rest on the exocervix such that the guide extends only 2 to 2.5 cm into the endocervical canal and does not enter the uterus.

The catheter is inserted into the guide such that the guide is positioned externally and coaxially to the catheter. The fit between the guide and catheter must be tight enough to prevent lavage fluid loss from the uterine cavity between the sleeve and the catheter. Accordingly, there is a snug fit with essentially no space between the catheter and sleeve. However, the catheter may be slid freely back and forth inside of the sleeve. The guide is characterized by a locator flange so that when inserted into the endocervical canal, the guide extends no more than between about 2 to 2.5 cm at an angulation of about 0° to 30°. Accordingly, the sleeve or guide never enters the uterus.

Ready entry of the catheter and guide of this invention into the endocervical canal is facilitated because (1) the uterine catheter has a blunt, preferably bullet-shaped, nose and (2) the guide provides a segmented rigidity to the catheter that is useful during insertion.

DESCRIPTION OF THE PREFERRED EMBODIMENTS

Figure 2:
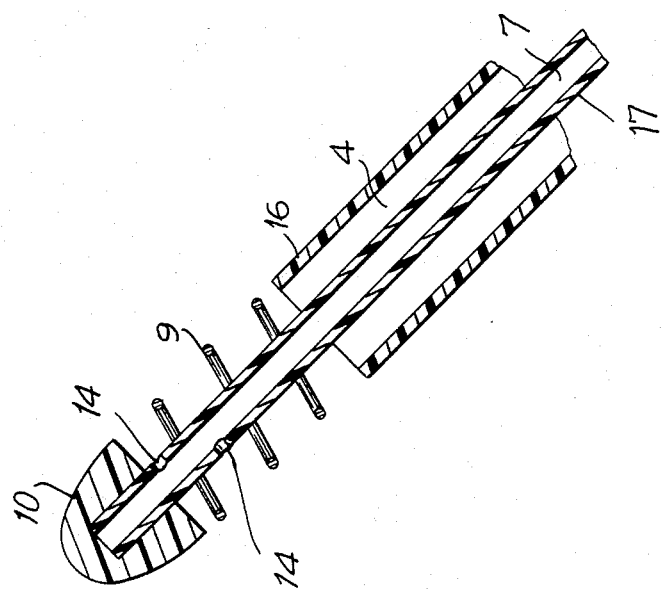
FIG. 2 is an enlarged elevational view of forward distal end of the catheter of FIG. 1.

Referring now to FIGS. 1 and 2, we have shown in elevational view one embodiment of an improved double lumen catheter (1) of this invention.

As shown in FIGS. 1 and 2, the catheter (1) comprises two lumens (4 and 7 in FIG. 2) defined by an external tube (16) and an internal tube (17), the tubes being coaxial to each other. The forward distal end of catheter (1) is adapted for insertion into the endocervical canal and endometrial cavity. It has a closed, rounded tip (10), the tip being attached to the forward distal end of the inner tube (17). The catheter (1) also comprises a cage (9) attached distally to the rounded tip (10) and proximally to the distal end of the external tube (16). The cage surrounds the distal end of the inner tube (17), which is coaxially located within it. The distal most end of the inner tube (17) has a number of radial spray holes (14) located in such a manner so as to prevent uterine lavage spray from hitting the structural members that define the cage.

The catheter also has a rear proximal end adapted to permit the separate connection of inner tube (17) and outer tube (16) to a fluid supply and recovery reservoir (12).

The catheter depicted in FIG. 1 has been inserted into a metal sleeve or guide (5) which is characterized by a locator flange (6) which is perpendicularly positioned on the sleeve so as to come to rest on the exocervix. In that position the guide extends not more than between about 2 to 2½ centimeters into the endocervical canal. The guide does not enter the uterus. As shown in FIG. 1, the guide also has an angulation between 0° to 30° to enable steering of the catheter within the uterus by rotation.

As shown in FIG. 1, the catheter also has a handle (15) and a slide (2) and manifold (3) which allow easy determination of the depth of insertion of the catheter into the uterine cavity and permit separate connection of the inner and outer tubes (16 and 17) to a fluid supply and reservoir (12). The catheter shown in FIG. 1 also includes a number of fittings (e.g., 8 and 11) which permit connection of the tubes separately to those supply and recovery vessels. The embodiment of FIG. 1 also permits the supply of fluid under positive pressure to the uterine cavity through holes (14) and the removal of substantially all of that fluid under negative pressure to the recovery vessel (12).

As shown in FIGS. 1 and 2, the cage (9) in the embodiment depicted is defined by the helical spring-like structure located around the distal most end of the inner tube (17). As illustrated in FIG. 2, the holes (14) and the structural members defining the cage (9) are located relative to each other such that the lavage spray from holes (14) does not hit the structural members.

In operation the improved catheter of this invention provides a fluid under positive pressure from a supply source to the uterine cavity. The positive pressure is preferably provided either by a syringe or a gravity feed. The catheter also allows recovery of substantially all of that fluid from the uterine cavity under negative pressure or gravity. The negative pressure is preferably caused by a motorized pump.

Having described the invention with particular reference to the preferred form thereof, it will be apparent to those skilled in the art to which the invention pertains after understanding the invention, that various changes and modifications may be made therein without departing from the scope of the invention as defined by the claims appended hereto.

I claim:

1. An improved uterine catheter which comprises (a) at least two lumens at the forward distal end defined by an external tube and at least one internal tube, the tubes being coaxial to each other; (b) a forward distal end adapted for insertion into the human cervical canal and endometrial cavity and having a closed, rounded tip, said tip being adjacent to the forward distal end of the internal tube; (c) a cage attached distally to said closed tip and proximally to the distal end of the external tube, the cage surrounding the distal most end of the internal tube which is located coaxially therein, said distal most end of the internal tube having a means for delivering lavage fluid to the uterine cavity; (d) a rear proximal end, said end being adapted to permit separate connection of the internal and external tubes to a fluid supply and a recovery reservoir; said catheter having an exterior diameter of about 7 to 16 French and having a combination of flexibility and stiffness sufficient to allow the catheter to describe a 10° to 30° angle per six centimeters when inserted into the uterine cavity, to conform to uterine contours and to be steerable within the uterine cavity.

2. The catheter according to claim 1, wherein there are two lumens defined by one external and one internal tube.

3. The catheter according to claim 1, wherein the tip is attached to the forward distal end of the internal tube.

4. The catheter according to claim 1, wherein the distal most end of the internal tube has a number of radial spray holes having a diameter of between 0.003 and 0.020 inches.

5. The catheter according to claim 4, wherein the radial spray holes are located adjacent to the point where the distal end of the internal tube is connected to the rounded tip.

6. The catheter according to claim 1, wherein said catheter is curved before insertion into said uterine cavity, said curve describing a 15° angle per six centimeters.

7. The catheter according to claim 1, wherein said catheter is curved before insertion into said uterine cavity, said curve describing a 10° to 30° angle per six centimeters.

8. The catheter according to claim 1, having an exterior diameter of 11 French.

9. A combination of the improved catheter of claim 1 and a rigid sleeve, said catheter being inserted snugly into said sleeve such that the sleeve is positioned externally and coaxially to the catheter, the sleeve being characterized by a locator flange that is positioned to come to rest on the exocervix so that the sleeve can extend no more than between about 2 to 2.5 cm into the endocervical canal.

10. The combination of catheter and sleeve according to claim 9, wherein said sleeve has an external diameter of about 8 to 17 French.

11. The combination of catheter and sleeve according to claim 9, wherein said sleeve has a length of about 10 to 14 cm.

12. The combination of catheter and sleeve according to claim 9, wherein said sleeve has an angulation of about 0° to 30°.

13. The catheter according to claim 1, made of a material which is polyvinyl chloride, polyethylene or tetrafluoroethylene.

14. The catheter according to claim 1, which is transparent.

15. The catheter according to claim 1, which is about 30 cm in length.

16. The catheter according to claim 1, wherein the tubes defining the lumens are made of a material which is tetrafluoroethylene, polyvinyl chloride or polyethylene.

17. The catheter according to claim 1, having a flexibility and stiffness defined as two inches of catheter clamped on one end deflecting at the free end 0.2 inches at loads ranging from 0.5 to 2.5 ounces.

* * * * *